United States Patent [19]
Lee et al.

[11] Patent Number: 5,959,151
[45] Date of Patent: Sep. 28, 1999

[54] PROCESS FOR THE PURIFICATION OF PENTAFLUOROPHENYL BORON COMPOUNDS

[75] Inventors: John Y. Lee; Steven P. Diefenbach; John M. Power; Ronny W. Lin, all of Baton Rouge, La.

[73] Assignee: Albemarle Corporation, Richmond, Va.

[21] Appl. No.: 09/058,408

[22] Filed: Apr. 9, 1998

[51] Int. Cl.[6] .................................................... C07F 5/02
[52] U.S. Cl. ..................................... 568/1; 568/6
[58] Field of Search ............................. 568/1, 6

[56] References Cited

U.S. PATENT DOCUMENTS

| | | | |
|---|---|---|---|
| 5,362,423 | 11/1994 | Ikeda et al. | 260/665 R |
| 5,399,780 | 3/1995 | Ikeda et al. | 568/1 |
| 5,473,036 | 12/1995 | Piotrowski et al. | 528/4 |
| 5,488,169 | 1/1996 | Ikeda et al. | 568/3 |
| 5,493,056 | 2/1996 | Ikeda et al. | 568/6 |
| 5,510,536 | 4/1996 | Ikeda et al. | 568/6 |
| 5,545,759 | 8/1996 | Ikeda et al. | 568/6 |
| 5,600,004 | 2/1997 | Diefenbach | 568/1 |

FOREIGN PATENT DOCUMENTS

| | | |
|---|---|---|
| 0604963 | 7/1994 | European Pat. Off. . |
| 0728760 | 8/1996 | European Pat. Off. . |
| 0728761 | 8/1996 | European Pat. Off. . |

OTHER PUBLICATIONS

CA:128:167512, abs in Angew Chem Int Ed Engl 36(24), pp.771–2774 by Karl, 1997.

*Primary Examiner*—Gary Geist
*Assistant Examiner*—Jean F Vollano
*Attorney, Agent, or Firm*—Philip M. Pippenger

[57] ABSTRACT

One aspect of the invention is a process for purifying a pentafluorophenyl boron compound from a crude mixture comprised of the pentafluorophenyl boron compound and impurities, the impurities at least comprised of an ether and water, the process comprising: (a) mixing the crude mixture with an azeotropic organic solvent which (i) is capable of azeotrope formation with the water and (ii) has a boiling point above the boiling point of the ether; (b) distilling the resulting solution to remove at least a portion of the impurities; and (c) cooling the distilled solution so that a precipitate comprised of the pentafluorophenyl boron compound is formed. Processes are also described for producing pentafluorophenyl boron compounds which are particularly pure, dry and fine.

42 Claims, No Drawings

PROCESS FOR THE PURIFICATION OF PENTAFLUOROPHENYL BORON COMPOUNDS

TECHNICAL FIELD

This invention pertains to novel processes for the isolation, purification and drying of pentafluorophenyl boron compounds and to the production of solid forms of such compounds having low water content (e.g., no more than about 500 ppm) and small average particle size (e.g., no more than about 200 microns).

BACKGROUND

Pentafluorophenyl boron compounds such as, e.g., bis-, tris- and tetra-kispentafluorophenyl boron derivatives are useful in forming olefin polymerization catalyst complexes with metallocenes. Processes for the production of such compounds have been disclosed, for example, in U.S. Pat. Nos. 5,488,169, 5,493,056, 5,510,536 and 5,545,759 to Ikeda et al., and 5,473,036 to Piotrowski, the disclosures of which are incorporated herein by reference. However, the known processes for isolating, purifying and drying these pentafluorophenyl boron compounds from crude reaction mixtures require large amounts of solvent, multiple reactors, long cycle times, and low temperatures of operation. Often such processes involve the use of aqueous solutions which introduce water impurities to the final product. The product is typically dried in vacuum to water levels of about 2000 ppm. However, even very small amounts (e.g., 1000 ppm) of water can drastically diminish the activity of the catalyst complexes. In addition, so far as is known, previous methods of producing solid forms of such compounds have resulted in products having excessive average particle sizes, thus requiring grinding or other additional processing to obtain a more advantageous average particle size.

A need therefore exists for a facile process for the isolation, purification and drying of crude wet mixtures comprised of pentafluorophenyl boron compounds. Additionally, a need exists for an efficient process for producing solid pentafluorophenyl boron compounds with an average particle size of no more than about 200 microns.

DESCRIPTION OF THE INVENTION

The present invention is deemed to satisfy these needs in a highly efficient way. In one embodiment, this invention provides a process for purifying a pentafluorophenyl boron compound from a crude mixture comprised of the pentafluorophenyl boron compound and impurities, the impurities at least being comprised of ether and water. The process comprises:

a) mixing the crude mixture with an azeotropic organic solvent which (i) is capable of azeotrope formation with the water and (ii) has a boiling point above the boiling point of the ether;

b) distilling the resulting solution to remove at least a portion of the impurities; and c) cooling the distilled solution so that a precipitate comprised of the pentafluorophenyl boron compound is formed.

This process enables isolation and purification of the pentafluorophenyl boron compound from the crude mixture in a single pot reaction, if desired. The crude mixture and the azeotropic organic solvent are mixed together in no particular order, and in fact may be simultaneously fed into one another, if desired. The weight ratio of pentafluorophenyl boron compound to azeotropic organic solvent in the mixture may range from about 1:1 to about 1:30, preferably from about 1:5 to about 1:15. The amount of azeotropic organic solvent used should be sufficient to permit chromophoric impurities in the crude mixture to dissolve into solution under the process conditions employed.

The resulting solution may be distilled at temperatures typically in the range of about 20° to about 150° C., preferably about 60° to about 110° C., and, if distilled under vacuum, more preferably about 22° C. to about 25° C. The distillation typically is conducted over a period of time sufficient to remove at least a portion of the impurities present in the crude mixture. Typically, distillation is conducted for a period of time in the range of about 1 to about 5 hours.

After distillation, the distilled solution (i.e., the solution which remains after the distillate is removed) is cooled to a temperature in the range of about −20° to about 120° C., preferably in the range of about 0° to about 60° C., and most preferably in the range of about 22° to about 25° C. A precipitate forms during this step, and may be removed from the solution by any conventional method, but is preferably removed by filtration. In this and all other processes of this invention, the recovered precipitate has a water content of no more than about 1000 ppm, preferably no more than about 500 ppm, and more preferably no more than about 100 ppm.

In another embodiment, the above-described process of this invention is modified so that an aliphatic hydrocarbon is mixed with the distilled solution while the solution is agitated. The aliphatic hydrocarbon may be mixed with the distilled solution while the solution is being cooled, or after the step of cooling has been completed. A precipitate which comprises the pentafluorophenyl boron compound is formed having an average particle size of no more than about 200 microns, more preferably no more than about 100 microns, and most preferably no more than about 25 microns. This process facilitates isolation, purification, drying, and particle size control in the same reaction vessel, if desired.

When mixing the aliphatic hydrocarbon with the distilled solution, the aliphatic hydrocarbon is preferably slowly added to the distilled solution over a period of about 1 to about 30 minutes, and as noted above the distilled solution is agitated during addition of the aliphatic hydrocarbon. Sufficient agitation is applied so that the average particle size of the resulting precipitate is no more than about 200 microns, more preferably no more than about 100 microns, and most preferably no more than about 25 microns. For commercial applications, the agitation preferably is provided by use of an industrial blender such as, e.g., a 3-speed, 4-liter, explosion-proof blender available from Waring, using a speed setting preferably in the range of about 15,500 to about 22,000 rpm for a period preferably of about 10 to about 60 minutes. The average particle size of the precipitate product resulting from this process will vary depending upon, and may be controlled by, the level of agitation applied to the solution.

This invention also provides a process for the production of a pentafluorophenyl boron compound having a particle size of no more than about 200 microns from a solution formed from a crude form of the pentafluorophenyl boron compound (e.g., one having particle size of more than about 200 microns) and an organic solvent, the process comprising (i) mixing an aliphatic hydrocarbon with the solution under an inert atmosphere and agitating the solution at a temperature in the range of about −20° to about 120° C., and (ii) recovering at least a portion of the pentafluorophenyl boron compound from the solution as precipitate. The aliphatic hydrocarbon and the solution are mixed together in no particular order, and in fact may be simultaneously fed together, if desired. The precipitate formed may be recovered from solution in any conventional manner, but is typically recovered by filtration. The crude form of the fluorinated aromatic boron compound will typically at least have chromophoric impurities which cause the compound to exhibit a color other than white. Through this process, such colorful impurities are dissolved into the organic solvent, where they remain during precipitation and recovery of the pentafluorophenyl boron compound. The resulting product is white in color, highly pure, and has an average particle size of no more than about 200 microns, more preferably no more than about 100 microns, and most preferably no more than about 25 microns. In a particularly preferred embodiment the pentafluorophenyl boron compound is N,N-dimethylanilinium tetrakis(pentafluorophenyl)borate, the weight ratio of organic solvent to aliphatic hydrocarbon is about 7:3, the temperature in mixing step (i) is in the range of about 22° to about 25° C., and mixing step (i) is performed over a period of time in the range of about 10 to 15 minutes. Under these conditions, the product is exceptionally pure, dry and fine.

The process conditions for all of the processes of this invention include use of substantially anhydrous, inert atmosphere such as dry nitrogen, argon, or the like. The processes of this invention are not particularly pressure dependent. The pressure used may be in the range of from about 0.1 to about 1500 mm Hg and preferably about 1.0 to about 1000 mm Hg. The more preferred pressures are atmospheric or near-atmospheric (700–800 mm Hg) pressures.

The pentafluorophenyl boron compound may include, for example, derivatives of bis(pentafluorophenyl)borane, tris(pentafluorophenyl)borane, or tetrakis(pentafluorophenyl)borate, including mixtures of any two or more of the foregoing. Non-limiting examples of such pentafluorophenyl boron compounds include N,N-dimethylanilinium tetrakis(pentafluorophenyl)borate, halomagnesium tetrakis(pentafluorophenyl)borate, tris(pentafluorophenyl)borane, lithium tetrakis(pentafluorophenyl)borate, triphenylcarbenium tetrakis(pentafluorophenyl)borate, and the like. In a particularly preferred embodiment, the pentafluorophenyl boron compound is a derivative of tetrakis(pentafluorophenyl)borate. Most preferably, the pentafluorophenyl boron compound is N,N-dimethyl-anilinium tetrakis(pentafluorophenyl)borate.

Suitable non-limiting examples of the ether present in the crude mixture containing the pentafluorophenyl boron compound include methyl ether, diethyl ether, dipropyl ether, butylmethyl ether, diisopropyl ether, dibutyl ether, diisoamyl ether, dioxane, tetrahydrofuran and the like, as well as mixtures of any two or more of the foregoing. In a preferred embodiment, the ether is diethyl ether. In addition to the pentafluorophenyl boron compound, ether and water, the crude mixture typically will contain other impurities. These impurities are often byproducts from the synthesis of the pentafluorophenyl boron compound. The impurities present can depend upon the particular synthesis process which was employed. Typical non-limiting examples of impurities which may be present in the crude mixture include hydrogen chloride, N,N-dimethylanilinium chloride, fluorinated impurities such as bromopentafluorobenzene, chloropentafluorobenzene, hexafluorobenzene, and organic impurities such as N,N-dimethylaniline, oxidized dimethylanilinium derivatives, and alyl halides.

The azeotropic organic solvent of this invention is capable of azeotrope formation with the water and has a boiling point above the boiling point of the ether. Suitable organic solvents include, for example, aliphatic hydrocarbons, aromatic hydrocarbons, alcohols, nitriles, esters, and ketones which are non-reactive with the pentafluorophenyl boron compound under the process conditions. Preferably, the azeotropic organic solvent is an aromatic hydrocarbon having 2 to 20 carbon atoms, and more preferably 5 to 10 carbon atoms. Non-limiting examples of suitable aromatic hydrocarbons include benzene, cumene, mesitylene, toluene, m-xylene, and the like, including mixtures of any two or more of the foregoing. In a particularly preferred embodiment, the azeotropic organic solvent is toluene.

The aliphatic hydrocarbon used in preferred embodiments may be one or more cyclic or acyclic hydrocarbons, and the aliphatic hydrocarbon may be the same or different from the azeotropic organic solvent of this invention. Suitable aliphatic hydrocarbons are those which reduce the solubility of the pentafluorophenyl boron compound in the solution, thereby facilitating precipitation of the pentafluorophenyl boron compound. Preferably, the aliphatic hydrocarbon has from 5 to 16 carbon atoms in the molecule. Non-limiting examples of suitable saturated aliphatic hydrocarbons include, n-pentane, n-hexane, n-heptane, n-octane, n-nonane, n-decane, n-undecane, n-dodecane, n-tridecane, n-tetra-decane, n-pentadecane, 2-methylpentane, 2,3-dimethylbutane, 2,4-dimethyl-5-butylnonane, cyclohexane and the like, including mixtures of any two or more of the foregoing. Less preferred are unsaturated aliphatic and cycloaliphatic hydrocarbons. Non-limiting examples of such unsaturated aliphatic and cycloaliphatic hydrocarbons include 1-pentene, 1-hexene, 1-heptene, 1-octene, 1-nonene, 1-decene, 1-undecene, 1-dodecene, 1-tridecene, 1-tetradecene, 1-pentadecene, 2-pentene, 3-hexene, 3,4-dimethyl-2-hexene, 1-hexyne, cyclohexene, and the like, including mixtures of any two or more of the foregoing unsaturated aliphatic hydrocarbons, or mixtures of any one or more of these unsaturated aliphatic hydrocarbons with any one or more of the foregoing saturated aliphatic hydrocarbons. More preferred are straight-chained saturated aliphatic hydrocarbons having 5 to 16 carbon atoms in the molecule. In a particularly preferred embodiment, the aliphatic hydrocarbon is n-pentane.

The organic solvent of this invention may include aromatic hydrocarbons, halogenated aliphatic hydrocarbons, halogenated aromatic hydrocarbons, esters, ketones and nitriles, so long as the pentafluorophenyl compound is soluble in the organic solvent. Non-limiting examples of suitable organic solvents include chlorobenzene, bromoform, chloroform, dichloromethane, nitrobenzene, dibromomethane, acetonitrile, acetone, and the like, including mixtures of any two or more of the foregoing. Halogenated aliphatic hydrocarbons having 1 to 20 carbon atoms are preferred. Halogenated aliphatic hydrocarbons having 1 to 6 carbon atoms are more preferred, with dichloromethane being particularly preferred.

As now may be appreciated, the processes of this invention require only a relatively small amount of process equipment in that all of the operations can be conducted in the same reaction vessel. In addition, this invention may be carried out as a batch, semi-continuous, or continuous process. Thus, if desired, each of the process steps may be conducted in a single reactor, such as a glass-lined reactor equipped with suitable distillation auxiliaries and agitators.

The following examples serve to illustrate this invention, but do not limit it.

EXAMPLE 1

Crude, wet N,N-dimethylanilinium tetrakis(pentafluorophenyl)borate ether solution (20.0 grams, 15.9 wt %) was charged to a 50 mL distillation reactor. A total of 8.0 grams of diethyl ether and ethyl bromide was removed from the crude by distillation at 35° C. (head temperature) and 53° C. (jacket temperature), under pressure of 760 mm Hg over a period of 1 hour. Toluene (14.2 grams) was then added, and an additional total of 6.3 grams of diethyl ether, ethyl bromide, pentafluorobenzene, and toluene (90.2, 2.4, 0.3 and 6.8 GC area %, respectively) was removed by distillation at 48–60° C. (head temperature) and 78–103° C. (jacket temperature) over a period of 1.3 hours using the same pressure. A two-layer solution then was observed in the reactor. Toluene (32.0 grams) was again added to the reactor, and a total of 32.4 grams of diethyl ether, pentafluorobenzene and toluene (0.53, 0.14, and 99.2 GC area %, respectively) was removed by distillation at 82–110° C. (head temperature), 117–125° C. (jacket temperature) over a period of 2 hours using the same pressure. Another 10.0 grams of toluene were then added to the reactor, and a total of 13.6 grams of toluene (99.77 GC area %) and diethyl ether (0.06 GC area %) was removed by distillation at 110° C. (head temperature), 125–131° C. (jacket temperature) over a period of 1 hour using the same pressure. The remaining solution was allowed to cool to 22–24° C. and then 12 grams of pentane was added to the solution. A precipitate formed and was removed from the solution by filtration. A total of 3.3 grams of slightly off-white precipitate was recovered and shown to contain 98% N,N-dimethylanilinium tetrakis(pentafluorophenyl)borate by NMR analyses. This precipitate was then redissolved in 37 grams of warm dichloromethane at 32° C., and the solution was then cooled to 22° C., at which time another 16 grams of pentane was added to the solution, while stirring. A white precipitate again formed and was removed from solution by filtration. After drying, the white precipitate weighed 3.0 grams (93.8% yield). By both F-NMR and H-NMR analysis (with trifluorobenzene internal standard), the white precipitate was determined to be 100% pure N,N-dimethylanilinium tetrakis(pentafluorophenyl)borate. Karl-Fisher analysis for water content showed 200 ppm of water present in the white precipitate, and the melting point of the white precipitate was determined by differential scanning calorimetry to be 225–226° C.

EXAMPLE 2

To a distillation reactor was charged 10 grams of a ether solution containing 1 part (i.e., 1.65+/−0.05 grams) of crude, wet N,N-dimethylanilinium tetrakis(pentafluorophenyl) borate, and 20 parts of toluene. The mixture was distilled at 110° C. (head), 125–134° C. (oil-bath) over a period of 3 hours, during which 16 parts of toluene, ether and water were removed. Then, 3 parts of pentane were added to the remaining solution (1 part N,N-dimethylanilinium tetrakis (pentafluorophenyl)borate and 4 parts toluene) and the solution was allowed to cool to 22° C. A precipitate of N,N-dimethylanilinium tetrakis(pentafluorophenyl)borate formed and was removed by filtration. The precipitate was rinsed with 3 parts pentane. Upon drying, the precipitate was determined to weigh 1.7 grams. Dichloromethane (18.0 grams) was then added to the precipitate and the mixture was warmed to 35° C. to dissolve the precipitate. Insoluble impurities were removed by filtration, and the solution was cooled to 22° C. Pentane (7.0 grams) was then added to the solution and a precipitate formed. The precipitate was removed by filtration and rinsed with 4 grams of pentane. Upon drying, the product weighed 1.5 grams (91+/−3% yield), and was snow-white in color. The product purity by F-NMR (with internal standard) was 101%. Purity by H-NMR (with internal standard) was 99%, with no ether present.

EXAMPLE 3

Crude N,N-dimethylanilinium tetrakis (pentafluorophenyl)borate (50.0 grams, 84% pure) was stirred in 500 grams of dichloromethane under nitrogen at 22° C. for 30–60 minutes. The solution exhibited a green color, and solid impurity was removed by filtration. Then, 100–150 grams of pentane was added slowly over a period of 10 minutes under nitrogen at 22° C. with stirring (using a magnetic bar). Fine N,N-dimethylanilinium tetrakis (pentafluorophenyl)borate precipitate was formed. The green impurity remained in solution. The precipitate was removed by filtration and was then rinsed with 100–150 grams of pentane. The yield of N,N-dimethylanilinium tetrakis(pentafluorophenyl)borate was approximately 95%, and the purity was 96+%.

EXAMPLE 4

Crude N,N-dimethylanilinium tetrakis (pentafluorophenyl)borate (50.0 grams, 84% pure) was stirred in 500 grams of dichloromethane under nitrogen at 22° C. for 30–60 minutes. The solution exhibited a green color, and solid impurity was removed by filtration. The remaining green solution was placed into an industrial blender. Then, 100–150 grams of pentane was added slowly over a period of 10 minutes under nitrogen at 22° C. with low-speed stirring. Fine N,N-dimethylanilinium tetrakis (pentafluorophenyl)-borate precipitate was formed. The green impurity remained in solution. The precipitate was removed by filtration and was then rinsed with 100–150 grams of pentane. The yield of N,N-dimethylanilinium tetrakis(pentafluorophenyl)borate was approximately 95%, and the purity was 96+%. The average particle size was approximately 22 microns.

Comparative Example

Crude, wet N,N-dimethylanilinium tetrakis (pentafluorophenyl)borate (1 gram), obtained by adding ether solution containing N,N-dimethylanilinium tetrakis (pentafluorophenyl)borate from the same source as that of Example 1 to an equal volume of hexane, was filtered, and then dried under vacuum to obtain dry N,N-dimethylanilinium tetrakis(pentafluorophenyl)borate. Karl-Fisher analysis for water content showed 2000 ppm of water present in the product, i.e., ten times the amount of water present in the product recovered in Example 1.

The novel processes of this invention enable the isolation, purification and drying of pentafluorophenyl boron compounds in high yields and purity, with very low water content and average particle sizes of preferably no more than about 200 microns, more preferably no more than about 100 microns, and most preferably no more than about 25 microns, all without the necessity of recrystallization, vacuum pumping or other additional, costly process steps.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for purifying a pentafluorophenyl boron compound from a crude mixture comprised of the pentafluorophenyl boron compound and impurities, the pentafluorophenyl boron compound being selected from the group consisting of bis(pentafluorophenyl) boron compound, a tris(pentafluorophenyl)boron compound, and a tetrakis (pentafluorophenyl)boron compound, the impurities at least comprised of an ether and water, the process comprising:
    a) mixing the crude mixture with an azeotropic organic solvent which (i) is capable of azeotrope formation with the water and (ii) has a boiling point above the boiling point of the ether;
    b) distilling the resulting solution to remove at least a portion of the impurities; and
    c) cooling the distilled solution so that a precipitate comprised of the pentafluorophenyl boron compound and having a water content of no more than about 1000 ppm is formed.

2. A process according to claim 1 further comprising the step of recovering the precipitate from the solution, the recovered precipitate having a water content of no more than about 500 ppm.

3. A process according to claim 1 wherein the ether is diethyl ether.

4. A process according to claim 1 wherein the azeotropic organic solvent is toluene.

5. A process according to claim 1 wherein the precipitate has a pentafluorophenyl boron compound purity of at least about 98%.

6. A process according to claim 1 wherein the pentafluorophenyl boron compound is a derivative of tetrakis (pentafluorophenyl)borate having at least a boron atom and a pentafluorophenyl group in the molecule.

7. A process according to claim 6 wherein the derivative of tetrakis(pentafluorophenyl)borate is N,N-dimethylanilinium tetrakis(pentafluorophenyl)borate.

8. A process according to claim 7 wherein the precipitate is recovered from the distilled solution has a water content of no more than about 500 ppm.

9. A process according to claim 8 wherein the precipitate has a water content of no more than about 100 ppm.

10. A process according to claim 9 wherein the precipitate has a N,N-dimethyl-anilinium tetrakis(pentafluorophenyl) borate purity of at least about 98%.

11. A process according to claim 10 wherein the ether is diethyl ether.

12. A process according to claim 11 wherein the azeotropic organic solvent is toluene.

13. A process for purifying a pentafluorophenyl boron compound from a crude mixture comprised of the pentafluorophenyl boron compound and impurities, the pentafluorophenyl boron compound being selected from the group consisting of a bis(pentafluorophenyl) boron compound, a tris(pentafluorophenyl)boron compound, and a tetrakis (pentafluorophenyl)boron compound, the impurities at least comprised of ether and water, the process comprising:
    a) mixing the crude mixture with an azeotropic organic solvent which (i) is capable of azeotrope formation with the water and (ii) which has a boiling point above the boiling point of ether;
    b) distilling the resulting solution to remove at least a portion of the impurities;
    c) cooling the distilled solution; and
    d) mixing an aliphatic hydrocarbon with the distilled solution and agitating the distilled solution;
whereby a precipitate comprised of the pentafluorophenyl boron compound is formed having an average particle size of no more than about 200 microns and having a water content of no more than about 1000 ppm.

14. A process according to claim 13 wherein steps c) and d) are performed concurrently.

15. A process according to claim 13 further comprising the step of recovering the precipitate from the distilled solution, the recovered precipitate having a water content of no more than about 500 ppm.

16. A process according to claim 13 wherein the ether is diethyl ether.

17. A process according to claim 13 wherein the azeotropic organic solvent is toluene.

18. A process according to claim 13 wherein the aliphatic hydrocarbon has from 5 to 16 carbon atoms in the molecule.

19. A process according to claim 13 wherein the average particle size is no more than about 100 microns.

20. A process according to claim 19 wherein the average particle size is no more than about 25 microns.

21. A process according to claim 13 wherein the pentafluorophenyl boron compound is a derivative of tetrakis (pentafluorophenyl)borate having at least a boron atom and a pentafluorophenyl group in the molecule.

22. A process according to claim 21 wherein the derivative of tetrakis(pentafluorophenyl)borate is N,N-dimethylanilinium tetrakis(pentafluorophenyl)borate, and wherein the average particle size is no more than about 25 microns.

23. A process according to claim 22 further comprising the step of recovering the precipitate from the distilled solution, the recovered precipitate having a water content of no more than about 500 ppm.

24. A process according to claim 23 wherein the ether is diethyl ether.

25. A process according to claim 23 wherein the azeotropic organic solvent is toluene.

26. A process according to claim 23 wherein the aliphatic hydrocarbon has from 5 to 16 carbon atoms in the molecule.

27. A process for the production of a pentafluorophenyl boron compound having an average particle size of no more than about 200 microns from a solution formed from a crude form of the pentafluorophenyl boron compound and an organic solvent in which the pentafluorophenyl boron compound is soluble, the pentafluorophenyl boron compound being selected from the group consisting of a bis (pentafluorophenyl) boron compound, a tris(pentafluorophenyl)boron compound, and a tetrakis(pentafluorophenyl)boron compound, the process comprising (i) mixing an aliphatic hydrocarbon with the solution under an inert atmosphere and agitating the solution at a temperature in the range of about −20° to about 120° C., and (ii) recovering at least a portion of the pentafluorophenyl boron compound from the solution as a precipitate having a water content of no more than about 1000 ppm.

28. A process according to claim 27 wherein the organic solvent is dichloromethane.

29. A process according to claim 27 wherein the average particle size is no more than about 100 microns.

30. A process according to claim 29 wherein the average particle size is no more than about 25 microns.

31. The process according to claim 27 wherein the pentafluorophenyl boron compound is a derivative of tetrakis(pentafluorophenyl)borate having at least a boron atom and a pentafluorophenyl group in the molecule.

32. A process according to claim 31 wherein the derivative of tetrakis(pentafluorophenyl)borate is N,N-dimethylanilinium tetrakis(pentafluorophenyl)borate, and wherein the average particle size is no more than about 25 microns.

33. A process according to claim 32 wherein the organic solvent is dichloromethane.

34. A process according to claim 32 wherein the precipitate has a water content of no more than about 500 ppm.

35. A process according to claim 32 wherein the weight ratio of organic solvent to aliphatic hydrocarbon is about 7:3, the temperature in step (i) is in the range of about 22° to about 25° C., and step (i) is performed over a period of time in the range of about 10 to 15 minutes.

36. A process according to claim 35 wherein the recovered precipitate is white and has a water content of no more than about 500 ppm.

37. The process according to claim 35 wherein the organic solvent is dichloromethane and the aliphatic hydrocarbon is pentane.

38. The process of claim 1, wherein the pentafluorophenyl boron compound is a halomagnesium tetrakis(pentafluorophenyl)borate.

39. The process of claim 1, wherein the pentafluorophenyl boron compound is lithium tetrakis(pentafluorophenyl)borate.

40. The process of claim 1, wherein the pentafluorophenyl boron compound is a tris(pentafluorophenyl)borane.

41. The process of claim 1, wherein the pentafluorophenyl boron compound is a triphenylcarbenium tetrakis(pentafluorophenyl)borate.

42. The process of claim 1, wherein the pentafluorophenyl boron compound is a bis(pentafluorophenyl)borane.

* * * * *